US012599385B2

(12) United States Patent
Iwasaki

(10) Patent No.: US 12,599,385 B2
(45) Date of Patent: Apr. 14, 2026

(54) ENDOSCOPE SYSTEM AND ENDOSCOPIC LIGATOR ATTACHMENT METHOD

(71) Applicant: OLYMPUS MEDICAL SYSTEMS CORP., Tokyo (JP)

(72) Inventor: Seiji Iwasaki, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 428 days.

(21) Appl. No.: 18/115,937

(22) Filed: Mar. 1, 2023

(65) Prior Publication Data

US 2023/0277180 A1 Sep. 7, 2023

Related U.S. Application Data

(60) Provisional application No. 63/315,767, filed on Mar. 2, 2022.

(51) Int. Cl.
| | |
|---|---|
| *A61B 1/00* | (2006.01) |
| *A61B 1/018* | (2006.01) |
| *A61B 17/12* | (2006.01) |

(52) U.S. Cl.
CPC .... *A61B 17/12013* (2013.01); *A61B 1/00101* (2013.01); *A61B 1/0014* (2013.01); *A61B 1/018* (2013.01)

(58) Field of Classification Search
CPC ............ A61B 1/00–32; A61B 1/00101; A61B 1/0014; A61B 1/018; A61B 1/00137; A61B 1/0009; A61B 1/00089; A61B 17/12013; A61B 17/12009; A61B 17/12; A61B 17/083; A61B 17/685; A61B 17/221; A61B 2017/00477; A61B 2018/00172

USPC ......... 600/104; 604/264, 523; 606/144, 139, 606/142, 148, 113
See application file for complete search history.

(56) References Cited

U.S. PATENT DOCUMENTS

| | | | | |
|---|---|---|---|---|
| 4,886,049 A | * | 12/1989 | Darras | ............... A61B 1/00142 |
| | | | | 600/125 |
| 5,897,487 A | * | 4/1999 | Ouchi | ............... A61B 1/00137 |
| | | | | 600/129 |
| 6,464,685 B1 | | 10/2002 | Suzuki et al. | |

(Continued)

FOREIGN PATENT DOCUMENTS

| | | |
|---|---|---|
| JP | 3514410 B2 | 3/2004 |
| JP | 5273980 B2 | 8/2013 |

OTHER PUBLICATIONS

Imaeda et al., "Advanced endoscopic submucosal dissection with traction", World Journal of Gastrointestinal Endoscopy, Jul. 26, 2014, vol. 6, Issue 7, pp. 286-295.

*Primary Examiner* — Anh T Nguyen
*Assistant Examiner* — James Edward Boice
(74) *Attorney, Agent, or Firm* — Morgan, Lewis & Bockius LLP

(57) ABSTRACT

An endoscope system of the disclosure includes an endoscope including an insertion section, and a coupling thread extending along the insertion section. The coupling thread includes a coupling portion at a distal end of the coupling thread, and a thread portion extending proximally from the coupling portion. The endoscope system includes a distal end cover on a distal end portion of the insertion section. At least a part of the distal end cover moves on an outer surface of the distal end portion. The distal end cover partially covers the coupling portion.

18 Claims, 10 Drawing Sheets

(56)             References Cited

U.S. PATENT DOCUMENTS

| | | | |
|---|---|---|---|
| 8,262,677 B2 | 9/2012 | Goto | |
| 2005/0033115 A1* | 2/2005 | Okada | A61B 1/00089 |
| | | | 600/104 |
| 2006/0258906 A1* | 11/2006 | Binmoeller | A61B 1/012 |
| | | | 600/114 |
| 2007/0088247 A1* | 4/2007 | Bliweis | A61B 1/00154 |
| | | | 606/21 |
| 2008/0242932 A1* | 10/2008 | Carter | A61B 1/00135 |
| | | | 600/127 |
| 2009/0125037 A1* | 5/2009 | Goto | A61B 17/12013 |
| | | | 606/140 |
| 2016/0192826 A1* | 7/2016 | Shimazaki | A61B 1/00137 |
| | | | 600/104 |
| 2016/0338723 A1* | 11/2016 | Gray | A61B 17/00234 |
| 2016/0361066 A1* | 12/2016 | Wolfe | A61B 1/00133 |
| 2018/0164582 A1* | 6/2018 | Kato | A61B 1/00163 |
| 2021/0219979 A1* | 7/2021 | Adar | A61B 1/00135 |

* cited by examiner

ENDOSCOPE SYSTEM AND ENDOSCOPIC LIGATOR ATTACHMENT METHOD

RELATED APPLICATION DATA

This application is based on and claims priority under 35 U.S.C. § 119 to U.S. Provisional Application No. 63/315, 767 filed on Mar. 2, 2022, the entire contents of which are incorporated herein by reference.

FIELD OF THE DISCLOSURE

The disclosure relates to an endoscope system that performs a predetermined treatment using an endoscope to which a predetermined treatment instrument is attached, and an endoscopic ligator attachment method.

BACKGROUND

These days, various treatments are performed on living tissue at a part in a body cavity of a subject by inserting an endoscope to which a predetermined treatment instrument is attached into the body cavity. The treatments that are performed in this case are generally performed by using various treatment instruments that are inserted through a treatment instrument insertion channel that is formed passing through an insertion section of the endoscope, for example. Such endoscopic treatments include a resection treatment of resecting a target part of living tissue inside the body cavity, and a hemostatic treatment of stopping bleeding at a bleeding part of living tissue inside the body cavity, for example.

Specific examples of the endoscopic treatment include endoscopic submucosal dissection (hereinafter referred to as "ESD treatment") and endoscopic variceal ligation (hereinafter referred to as "EVL treatment"), for example. These various endoscopic treatments are performed by attaching, to an endoscope, a treatment instrument adapted to a respective treatment. Accordingly, conventionally, various proposals have been made with respect to an endoscopic ligator as a treatment instrument that is used by being attached to an endoscope, and an endoscope system to which such an endoscopic ligator and the like may be attached, as disclosed in Japanese Patent No. 5273980 and Japanese Patent No. 3514410, for example.

For example, the EVL treatment is a procedure that is mainly performed at a time of medical treatment for removing esophageal varices. At the time of a procedure accompanying the EVL treatment, first, a treatment target part is specified by using an endoscope, by observing surroundings of living tissue that is a medical treatment target inside a body cavity. At the time of performing the EVL treatment on the target part, an insertion section of the endoscope is temporarily removed from the body cavity. Then, an EVL device (an endoscopic ligator) is attached to the endoscope that is removed. Then, the endoscope to which the EVL device (the endoscopic ligator) is attached is inserted again into the body cavity of the subject. Then, a distal end portion of the insertion section is guided to the treatment target part, and a treatment (the EVL treatment) is performed on the treatment target part. Such a series of processes is usually performed at the time of performing the EVL treatment.

In this case, at the time of attaching the EVL device (the endoscopic ligator) to the endoscope, a plurality of burdensome tasks as mentioned below have to be performed, for example:

(1) a task of inserting an operation wire in a treatment instrument insertion channel of an insertion section of the endoscope, (2) a task of attaching a distal end head member to a distal end portion of the insertion section of the endoscope, (3) a task of coupling a proximal end of the operation wire to a winder, and (4) a task of attaching the winder to an operation section of the endoscope.

SUMMARY OF THE DISCLOSURE

An endoscope system includes: an endoscope including an insertion section; a coupling thread extending along the insertion section, the coupling thread including; a coupling portion at a distal end of the coupling thread, and a thread portion extending proximally from the coupling portion; and a distal end cover on a distal end portion of the insertion section, wherein at least a part of the distal end cover moves on an outer surface of the distal end portion, wherein the distal end cover partially covers the coupling portion.

An endoscopic ligator attachment method, comprises: inserting a coupling thread through an insertion section of an endoscope, wherein the coupling thread includes a partial region at a distal end side; attaching the partial region of the coupling thread to a distal end portion of the insertion section by a distal end cover; moving the distal end cover relative to the distal end portion to release the partial region of the coupling thread from the distal end portion; and coupling the distal end side of the coupling thread and a distal end head of the endoscopic ligator to each other.

An endoscope system comprises: an endoscope including an insertion section, wherein the insertion section includes a distal end portion and wherein the distal end portion includes a groove configured to receive a coupling thread; and a distal end cover provided on the distal end portion of the insertion section, wherein at least a part of the distal end cover moves on an outer surface of the distal end portion, wherein the distal end cover includes a cutout portion, wherein an area of the cutout portion is a first area, an area of the groove is a second area, and a size of the first area is equivalent to or larger than a size of the second area, and wherein the distal end partially covers the coupling portion.

DETAILED DESCRIPTION

Figure 1:
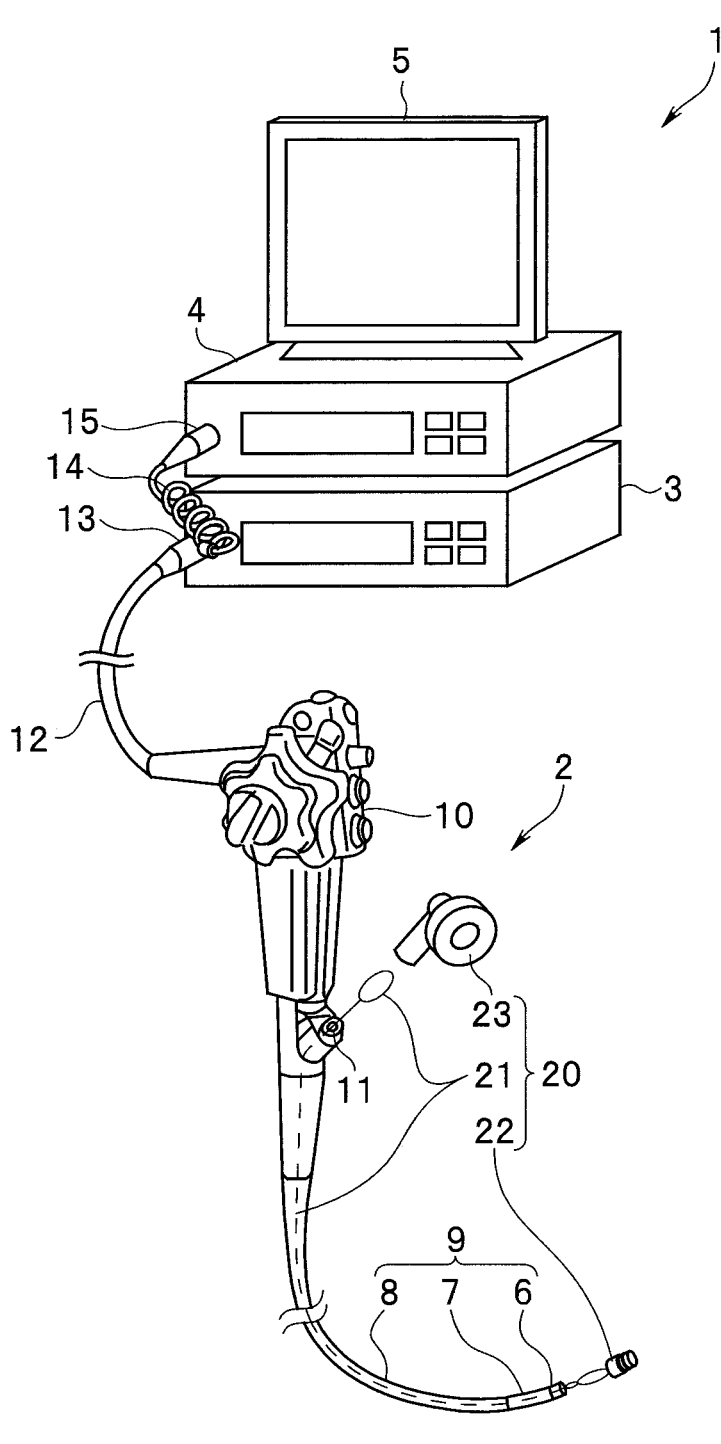
FIG. 1 is a schematic overall diagram showing an endoscope system of an embodiment of the present disclosure.

As described above, generally, to perform an EVL treatment, an endoscope that is being used to perform observation inside a body cavity is temporarily removed from the body cavity, and an EVL device (an endoscopic ligator) is attached to the endoscope. For example, at this time, a task of passing an operation wire through a treatment instrument insertion channel of the endoscope has to be performed, as described above.

However, in a case where there is a possibility of contamination around an opening on a distal end side of the treatment instrument insertion channel of the endoscope or inside the treatment instrument insertion channel, there is a problem that the task of passing the operation wire through the treatment instrument insertion channel becomes more difficult compared to a usual case where there is no contamination.

As described above, with a conventional endoscope system, various treatment instruments can be attached to the endoscope, and the attachment task may be burdensome and may take time. Treatment, medical treatment and the like may be interrupted and increased.

However, with conventional endoscope systems disclosed in Japanese Patent No. 5273980 mentioned above and Japanese Patent No. 3514410 mentioned above, for example, reduction in burden of attaching various treatment instruments and reduction in time necessary for attachment is not fully considered.

According to an embodiment of the present disclosure described below, there may be provided an endoscope system that has a configuration with which a task of attaching a predetermined treatment instrument to an endoscope may be simplified and that may contribute to reduction in burden at the time of attaching the treatment instrument to the endoscope and to reduction in time necessary for such attachment, and an endoscopic ligator attachment method.

Hereinafter, the present disclosure will be described using an embodiment shown in the drawings. Note that each diagram used in the description below is schematic, and a dimensional relationship, scales and the like of respective members may be shown differently for each structural component in order to allow each structural element to be shown large enough to be recognized in the drawings. Accordingly, the present disclosure is not limited to a mode shown in the drawings with respect to the number of pieces of each structural component, the shape of each structural component, a ratio of sizes of respective structural components, relative positional relationships of respective structural components, and the like shown in each drawing.

Figure 2:
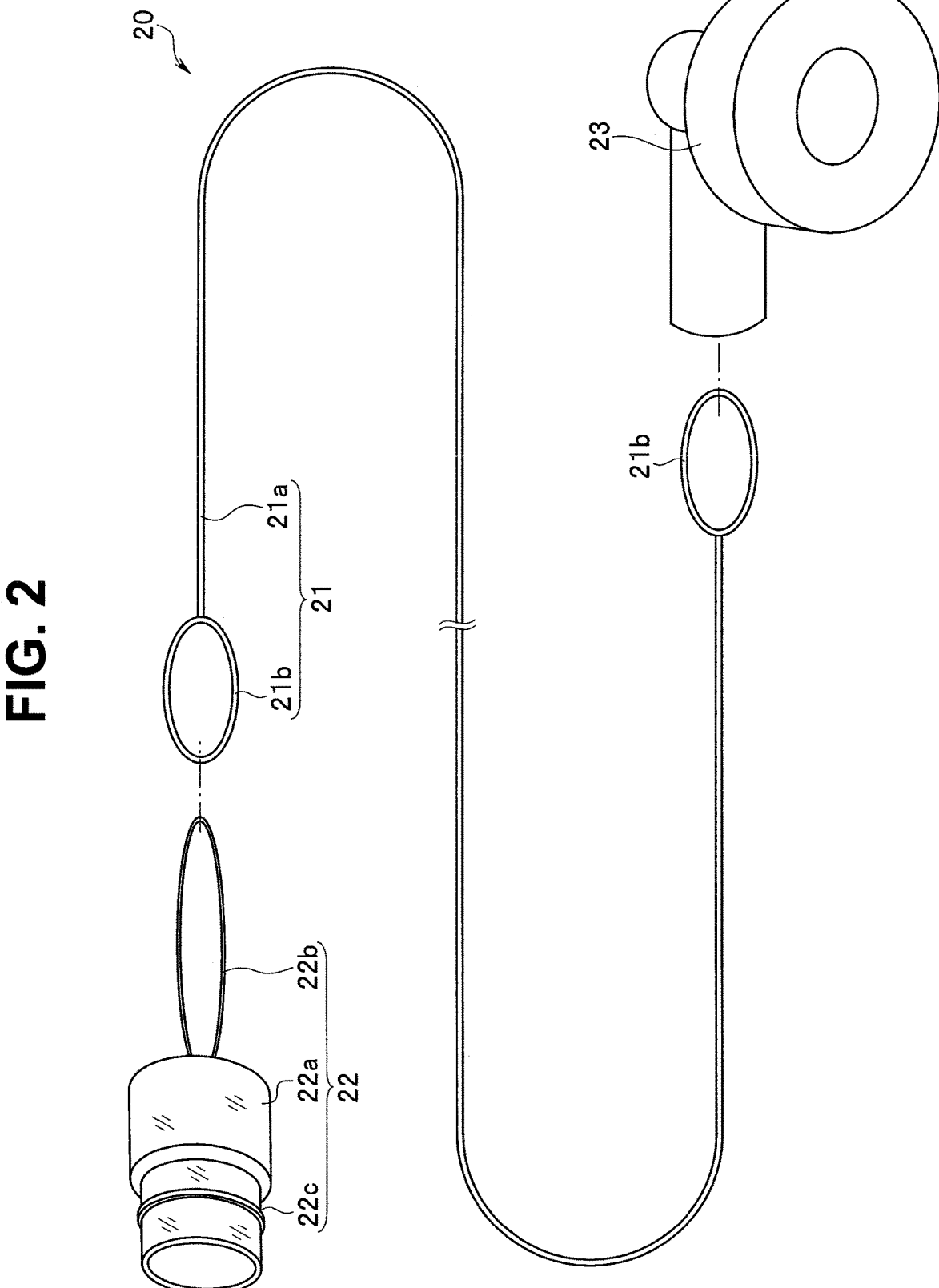
FIG. 2 is a schematic configuration diagram of an endoscopic ligator that is attached to the endoscope system of the embodiment of the present disclosure.

First, a configuration of an endoscope system of an embodiment of the present disclosure will be described with reference to FIGS. 1 and 2. FIG. 1 is a schematic overall diagram showing an endoscope system of an embodiment of the present disclosure. FIG. 2 is a schematic configuration diagram of an endoscopic ligator as a treatment instrument that is attached to the endoscope system of the embodiment of the present disclosure.

In the present embodiment, a description will be given citing as an example an endoscope system for performing an EVL treatment. A basic configuration of an endoscope system 1 shown in FIG. 1 is substantially the same as a configuration of a conventional endoscope system. Accordingly, a description given below is simply an outline of each structural member of the endoscope system 1.

As shown in FIG. 1, the endoscope system 1 of the present embodiment includes an endoscope 2, a light source device 3, a video processor 4, a display device 5, an endoscopic ligator 20, and the like.

The endoscope 2 includes an insertion section 9 that is substantially a long, thin tube, an operation section 10, a universal cord 12, and the like.

The insertion section 9 is formed from a distal end portion 6, a bending portion 7, and a flexible tube portion 8 that are continuously provided in such an order from a distal end side. The insertion section 9 is thus formed to have a shape of a substantially long, thin tube as a whole. The operation section 10 is connected to a proximal end portion of the insertion section 9. As will be described later in detail, the endoscopic ligator 20 is removably provided at the endoscope 2.

An image pickup unit, an illumination unit and the like that are not shown are provided inside the distal end portion 6. Note that an internal configuration of the distal end portion 6 is substantially the same as a configuration of a distal end portion of a conventional endoscope. Accordingly, detailed description and illustration of the internal configuration of the distal end portion 6 are omitted.

The operation section 10 includes an operation section main body, a plurality of operation members, a forceps port 11, and the like. The operation section main body is substantially box-shaped as a whole, and forms a grasping portion. As described above, the insertion section 9 is provided extending from the operation section main body. The plurality of operation members are operation members for performing various operations of the endoscope 2. The plurality of operation members are provided at predetermined positions on an outer surface of the operation section main body.

The forceps port 11 is provided at a predetermined position on the operation section main body of the operation section 10. The forceps port 11 includes an opening for allowing insertion of various treatment instruments and the like (not shown). Furthermore, the forceps port 11 is a proximal end side opening of a treatment instrument insertion channel (see reference sign 33a in FIG. 3; described later) that is formed passing through from the operation section 10 to a distal end side opening (see reference sign 33 in FIG. 3; described later) of the distal end portion 6 of the insertion section 9. One end of a coupling thread 21 of the endoscopic ligator 20 is disposed in the forceps port 11.

The universal cord 12 is a tubular member that extends from a side of the operation section 10. A scope connector 13 is provided at a distal end of the universal cord 12. The scope connector 13 is connected to the light source device 3.

The light source device 3 is a device configured to supply illumination light to an optical illumination system or an illumination device (not shown) provided inside the distal end portion 6 of the insertion section 9 of the endoscope 2. Illumination light emitted from the light source device 3 is transmitted from the light source device 3 to the distal end portion 6 of the insertion section 9 of the endoscope 2, through an optical fiber cable or the like (not shown) that is disposed passing through the universal cord 12, the operation section 10, and the insertion section 9 from the scope connector 13. The illumination light passes through an optical illumination member (see reference sign 32 in FIG. 3; described later) provided on a front surface of the distal end portion 6, and is emitted toward an observation target object in front of the distal end portion 6.

Note that a configuration for transmitting illumination light from the light source device 3 to the distal end portion 6 through the optical fiber cable or the like is illustrated as an example of the illumination device, but such a configuration is not restrictive. For example, a configuration is also possible where an LED (light emitting diode) or the like as an illumination light source is provided inside the distal end portion 6, and light emission by the illumination light source (LED) is controlled by the light source device 3.

A scope cable 14 extends sideways from the scope connector 13. An electrical connector section 15 is provided at a distal end of the scope cable 14. The electrical connector section 15 is connected to the video processor 4.

The video processor 4 is a control device configured to control the entire endoscope system 1. In this case, the video processor 4 includes a signal processing circuit that is configured to receive an image pickup signal from the image pickup unit (not shown) provided inside the distal end portion 6 of the insertion section 9 of the endoscope 2 and to perform predetermined signal processing, and a control processing circuit that is configured to output a control signal for driving the image pickup unit, for example.

The video processor 4 and the image pickup unit are electrically connected by a signal transmission cable (not shown). For this purpose, the signal transmission cable is disposed passing from the electrical connector section 15 through the universal cord 12, the operation section 10, and the distal end portion 6 of the insertion section 9. According to such a configuration, the image pickup signal outputted from the image pickup unit, the control signal outputted from the video processor 4, and the like are transmitted between the image pickup unit and the video processor 4 through the signal transmission cable. Note that a composite cable that is a bundle of cables covered by an outer skin shield, an outer skin tube or the like is adopted as a mode of the signal transmission cable, for example.

The video processor 4 and the display device 5 are connected by a video cable (not shown). The video cable transmits an image signal, the control signal and the like outputted from the video processor 4 to the display device 5.

The display device 5 receives the image signal and the control signal outputted from the video processor 4, and displays an endoscope image in a predetermined format based on a display mode according to the control signal that is received, various information and the like.

With the endoscope system 1 of the present embodiment, the endoscopic ligator 20 is removably provided at the endoscope 2. The endoscopic ligator 20 includes the coupling thread 21 that is an operation wire, a distal end head 22 that is a distal end structural member, a winder 23, and the like.

The coupling thread 21 is an operation wire that is provided along the insertion section 9 of the endoscope 2. The present embodiment shows an example where the coupling thread 21 is provided inserted through the treatment instrument insertion channel of the insertion section 9 of the endoscope 2. The coupling thread 21 is a member that is used to operate, from a hand side of the endoscope 2, an O-shaped ring 22c for ligation (see FIG. 2) provided on the distal end head 22 (described in detail later) of the endoscopic ligator 20.

As shown in FIG. 2, the coupling thread 21 is formed from a thread portion 21a and a coupling portion 21b. The thread portion 21a is formed from resin, metal material, fiber material or the like that is thread-shaped, that has a small diameter and predetermined strength, and that is flexible. As for the coupling thread 21, a material that does not extend nor contract can be used. Note that the coupling thread 21 itself is substantially the same as a thread-shaped member that is generally used in conventional medical devices such as an endoscopic ligator.

The coupling portion 21b is ring-shaped, for example, and is integrally formed with the thread portion 21a, at one end portion or both end portions of the thread portion 21a. In other words, the coupling portion 21b is formed as a partial region on a distal end or a partial region on a proximal end of the coupling thread 21. Note that in this case, the coupling portion 21b is made from the same material as the thread portion 21a. The coupling portion 21b illustrated in the present embodiment is formed into a loop shape by forming a thread-shaped material the same as the thread-shaped material of the thread portion 21a.

Note that FIG. 2 shows an example where the coupling portion 21b is provided at both ends of the coupling thread 21, but such an example is not restrictive. The coupling portion 21b is provided at least on a distal end side of the coupling thread 21.

Furthermore, the shape of the coupling portion 21b is not limited to the shape described above. Although not shown, the coupling portion 21b may be formed to have a hook shape, for example. In this case, the coupling portion 21b is formed to have certain rigidity. The hook shape has to be maintained even when predetermined tension is applied to the coupling portion 21b. Especially, the hook shape is not deformable even when the coupling member 21b is pulled into the treatment instrument insertion channel.

The thread portion 21a of the coupling thread 21 is disposed passing through the treatment instrument insertion channel of the insertion section 9 of the endoscope 2. At this time, the coupling portion 21b on the distal end side of the coupling thread 21 is disposed at a position extending forward from a distal end opening of the treatment instrument insertion channel (see reference sign 33 in FIG. 3) of the distal end portion 6 of the insertion section 9 of the endoscope 2. At this time, the coupling portion 21b on a proximal end side of the coupling thread 21 is disposed at a position extending to outside from the forceps port 11 of the operation section 10 of the endoscope 2 (see FIG. 7; described later).

Figure 9:
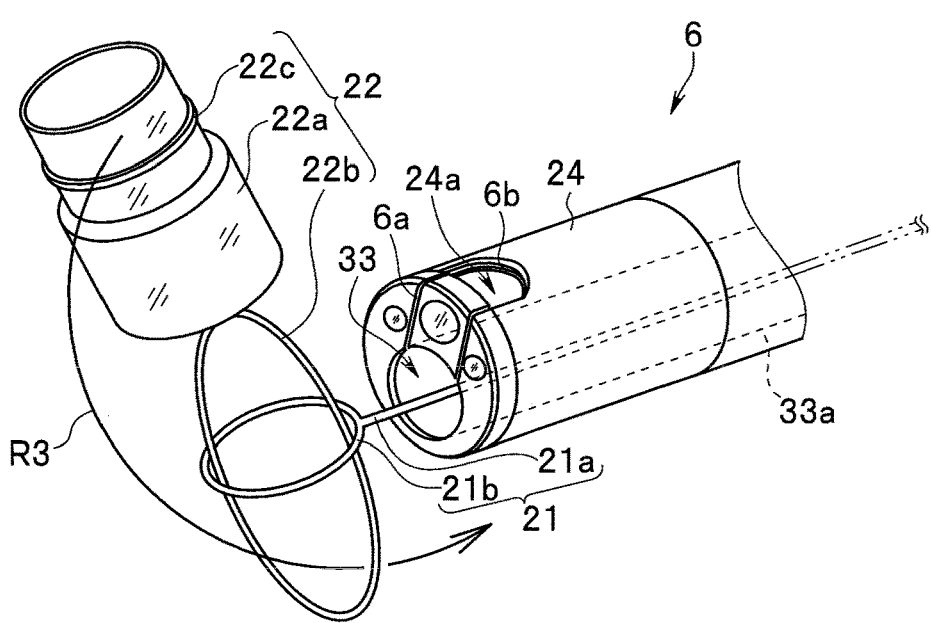
FIG. 9 is a schematic perspective view showing a manner of coupling a distal end head to the coupling thread.
Figure 10:
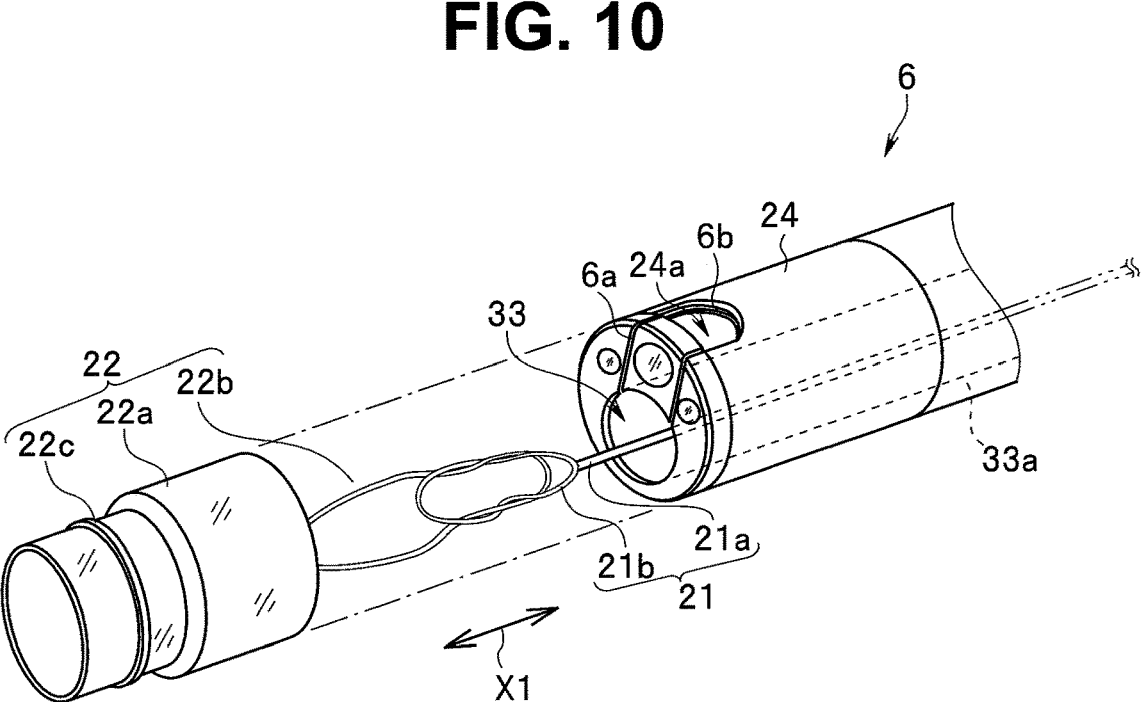
FIG. 10 is a schematic perspective view showing a manner of attaching the distal end head to the distal end portion of the endoscope.

At the time of use of the endoscopic ligator 20, the coupling portion 21b on the distal end side of the coupling thread 21 is coupled to the distal end head 22 (see FIGS. 9 and 10; described later). At the time of use, the coupling portion 21b on the proximal end side of the coupling thread 21 is coupled to the winder 23 (see FIGS. 11 and 12; described later). Note that the time of use of the endoscopic ligator 20 refers to a time during performance of the EVL treatment (the same applies in the following description).

At a time of non-use of the endoscopic ligator 20, the coupling portion 21b on the distal end side of the coupling thread 21 is fixed to the distal end portion 6 of the insertion section 9 of the endoscope 2 (described in detail later; see FIG. 6 and the like). At the time of non-use, the coupling portion 21b on the proximal end side of the coupling thread 21 is fastened at an external region of the forceps port 11 (described in detail later; see FIG. 8 and the like), for example. Note that the time of non-use of the endoscopic ligator 20 refers to a state where the endoscopic ligator 20 (structural members other than the coupling thread 21) is not attached to the endoscope 2, such as a time of normal use of the endoscope 2 (during observation of inside of a body cavity) or a time when the endoscope 2 is stored (the same applies in the following description).

The distal end head 22 is a distal end structural member of the endoscopic ligator 20. The distal end head 22 includes a main body portion 22a, a coupling portion 22b, the O-shaped ring 22c for ligation, and the like.

The main body portion 22a is a member that includes an opening on both ends, and that is formed into a cylindrical shape using a transparent resin member or the like, for example. At the time of use of the endoscopic ligator 20, the main body portion 22a is attached to a distal end of the distal end portion 6 of the insertion section 9 of the endoscope 2. The O-shaped ring 22c for ligation is provided on an outer periphery surface close to a distal end of the main body portion 22a. Furthermore, a disengaging mechanism (not shown) configured to disengage the O-shaped ring 22c for ligation from the distal end of the main body portion 22a is provided inside the main body portion 22a.

The coupling portion 22b is a member forming a part of the disengaging mechanism inside the main body portion 22a. The coupling portion 22b is a member that is coupled to the coupling portion 21b on the distal end side of the coupling thread 21 at the time of use of the endoscopic ligator 20 to couple the distal end head 22 to the coupling thread 21. According to such a configuration, in the case where the coupling thread 21 is pulled in an insertion axis (longitudinal axis) direction from the hand side at the time of use of the endoscopic ligator 20, for example, the coupling thread 21 pulls the coupling portion 22b in the same direction. Tension is thus transmitted to the disengaging mechanism. At this time, the disengaging mechanism disengages the O-shaped ring 22c for ligation from the distal end of the main body portion 22a.

The O-shaped ring 22c for ligation is a member that is used, at the time of use of the endoscopic ligator 20, to perform a ligation treatment on a target part. As described above, the O-shaped ring 22c for ligation is provided on an outer periphery close to the distal end of the main body portion 22a. Furthermore, the O-shaped ring 22c for ligation is coupled to the disengaging mechanism by a structure that is not shown.

The winder 23 is an operation member that is removably disposed on the forceps port 11 of the operation section 9 of the endoscope 2. The winder 23 is attached to the forceps port 11 at the time of use of the endoscopic ligator 20. At this time, the coupling portion 21b on the proximal end side of the coupling thread 21 is coupled to the winder 23. A configuration is adopted according to which the coupling thread 21 is wound around when a surgeon performing a treatment performs a predetermined operation on the winder 23 at a predetermined timing. The winder 23 transmits the tension to the disengaging mechanism of the distal end head 22 through the coupling thread 21 by such a configuration.

The basic configuration of the endoscopic ligator 20 itself configured in the above manner is substantially the same as the configuration adopted by a conventional endoscopic ligator. A difference from the conventional endoscopic ligator is that the coupling thread 21, the distal end head 22, and the winder 23 of the endoscope system 1 of the present embodiment are formed as separate bodies. Moreover, with the endoscope system 1 of the present embodiment, the coupling thread 21 is disposed passing through the treatment instrument insertion channel 33a (see FIG. 3) of the insertion section 9 of the endoscope 2 at all times. At the time of use of the endoscopic ligator 20, the coupling thread 21 and the distal end head 22 may be easily coupled to each other, and at the same time, the coupling thread 21 and the winder 23 may be easily coupled to each other.

With the coupling thread 21 of the endoscope system 1 of the present embodiment, at the time of non-use of the endoscopic ligator 20, the thread portion 21a is disposed passing through the treatment instrument insertion channel, and the coupling portion 21b on the distal end side is fixed to the distal end portion 6. The detailed configuration of the distal end portion 6 for this purpose is described below with reference to FIGS. 3 to 6.

Figure 3:
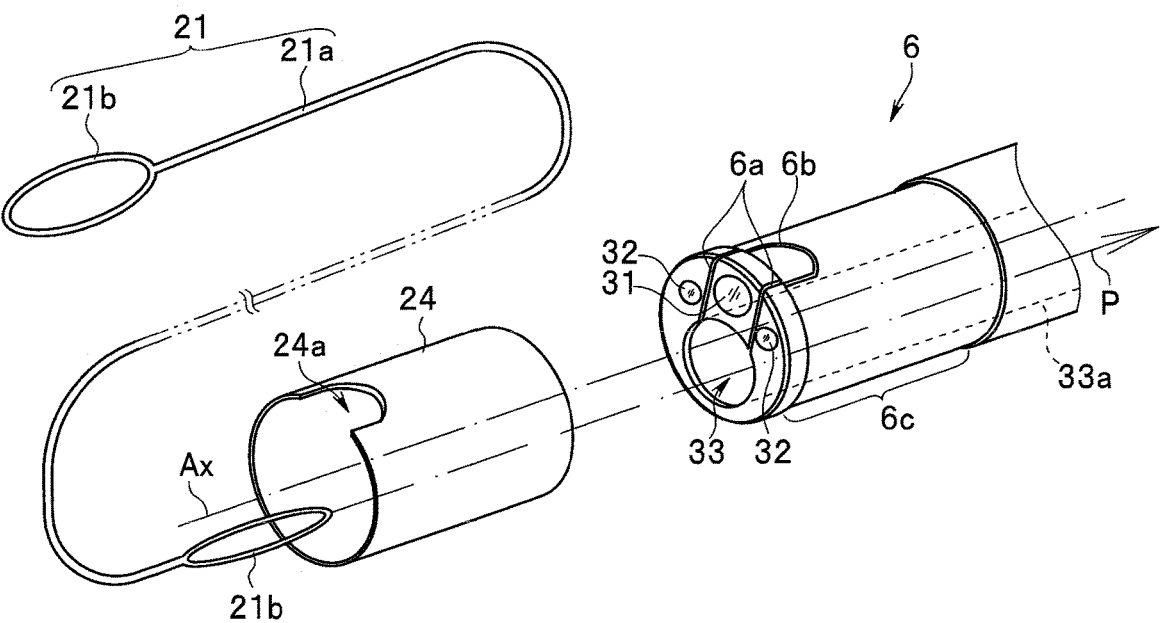
FIG. 3 is an enlarged exploded perspective view of main parts showing, in an exploded and enlarged manner, a configuration of a distal end portion of an endoscope of the endoscope system of the present embodiment.
Figure 4:
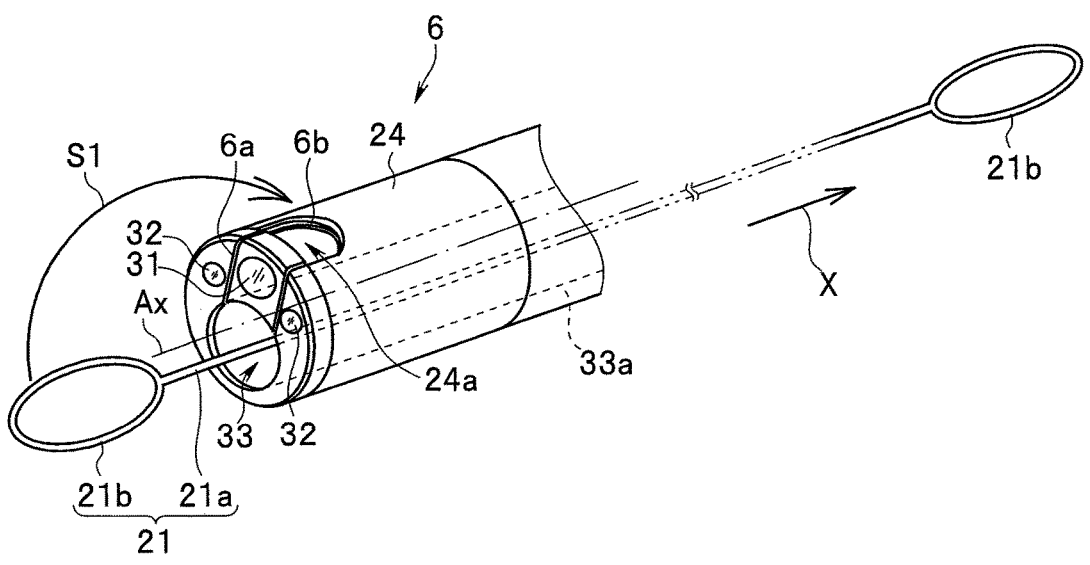
FIG. 4 is a schematic perspective view showing assembling of each structural member of the distal end portion shown in FIG. 3 (a coupling-thread non-fixed state).
Figure 5:
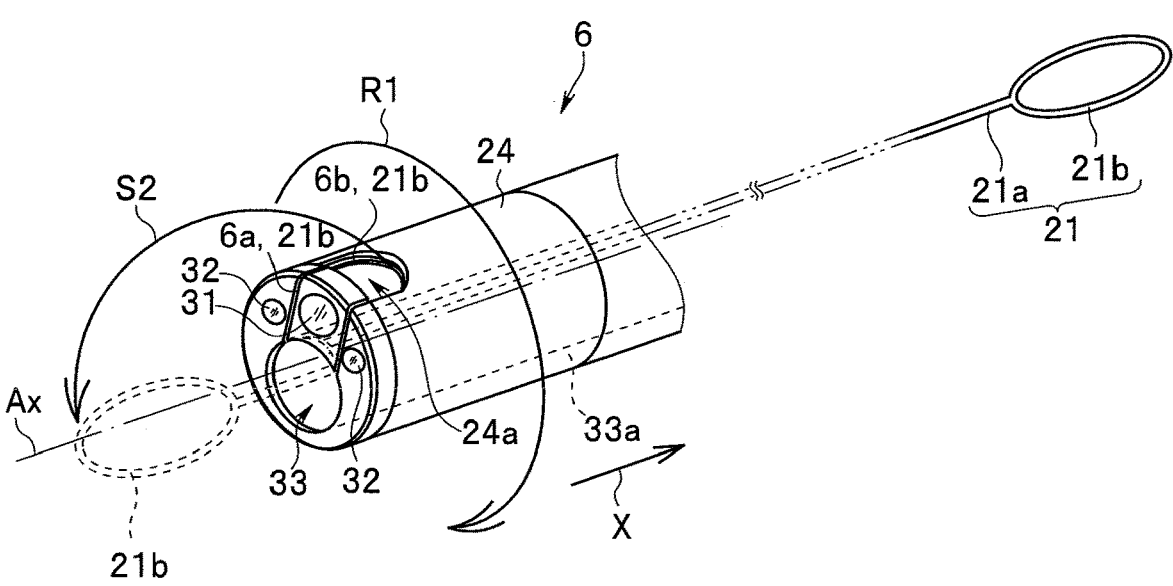
FIG. 5 is a schematic perspective view showing a state after a state shown in FIG. 4, where a coupling member of a coupling thread is fitted in a groove on the distal end portion.

FIG. 3 is an enlarged exploded perspective view of main parts showing, in an exploded and enlarged manner, a configuration of the distal end portion of the endoscope of the endoscope system according to the present embodiment. FIGS. 4 and 5 are schematic perspective views showing assembling of each structural member of the distal end portion shown in FIG. 3. Of the drawings, FIG. 4 shows a state where a distal end cover is attached to an outer periphery of the distal end portion, and where the coupling thread is inserted through the treatment instrument insertion channel (the coupling thread is in an unfixed state). FIG. 5 shows a state after the state shown in FIG. 4, where the coupling portion of the coupling thread is fitted in a groove on the distal end portion. FIG. 6 is a schematic perspective view showing an assembly completion state of the distal end portion (the coupling thread is in a fixed state).

As shown in FIGS. 3 to 6, an observation window 31, illumination windows 32 (two pieces), a channel opening 33 and the like are provided in a distal end surface of the distal end portion 6 of the insertion section 9 of the endoscope 2 of the endoscope system 1 according to the present embodiment.

The observation window 31 is a light transmissive optical member forming a part of an observation optical system (not shown). The observation optical system is a structural member including a function of forming an optical image of an observation target object. An image pickup device and the image pickup unit including a drive circuit, the signal processing circuit and the like are disposed behind the observation optical system.

The illumination window 32 is a light transmissive optical member forming a part of an illumination optical system or the illumination device (not shown). The illumination window 32 is a structural member including a function of radiating, toward an observation target object in front of the distal end portion 6, a light beam transmitted from the light source device 3 or a light beam emitted from the illumination light source. Note that an example configuration is described with respect to the endoscope 2 of the present embodiment, where the illumination windows 32 are provided at respective positions that are substantially opposite to each other across the observation window 31.

The channel opening 33 is a structural part that serves both as a distal end side opening of the treatment instrument insertion channel 33a and as a suction opening. The coupling thread 21 is disposed from the channel opening 33 to the forceps port 11 through the treatment instrument insertion channel 33a. Note that the state shown in FIG. 3 shows a state before the coupling thread 21 is inserted through the treatment instrument insertion channel 33a. Reference sign P in FIG. 3 indicates a direction in which the coupling thread 21 is inserted through the treatment instrument insertion channel 33a.

Grooves (6a, 6b) where the coupling portion 21b that is a partial region on the distal end of the coupling thread 21 is to be fitted are provided on the distal end portion 6. The present embodiment shows an example where the grooves (6a, 6b) are provided on a side surface and the distal end surface of the distal end portion 6. The groove that is provided on the distal end surface of the distal end portion 6 will be indicated by reference sign 6a, and will be referred to below as a distal end groove 6a. The groove that is provided on the side surface of the distal end portion 6 will be indicated by reference sign 6b, and will be referred to below as a side surface groove 6b.

Two distal end grooves 6a are formed on the distal end surface of the distal end portion 6, extending between a side edge of a treatment instrument insertion channel opening 33 and an outer periphery edge portion of the distal end portion 6. The side surface groove 6b is formed by extending the two distal end grooves 6a on an outer periphery surface of the distal end portion 6 in a direction along an insertion axis Ax and by a predetermined length and connecting the two at a predetermined position. According to such a configuration, the distal end grooves 6a and the side surface groove 6b may be disposed while allowing fitting of the coupling portion 21b on the distal end side of the coupling thread 21. Accordingly, width and depth of each of the distal end grooves 6a and the side surface groove 6b are set to sizes that are substantially equivalent to or slightly larger than a diameter of a thread-shaped material forming the coupling portion 21b.

Moreover, a distal end cover 24 that covers a region extending over a predetermined range on the outer periphery surface is provided on the distal end portion 6. The distal end cover 24 includes an opening on both ends, and is formed to have a substantially cylindrical shape as a whole. The distal end cover 24 is formed using a material that is flexible and that is capable of extending and contracting, such as silicone rubber.

Figure 6:
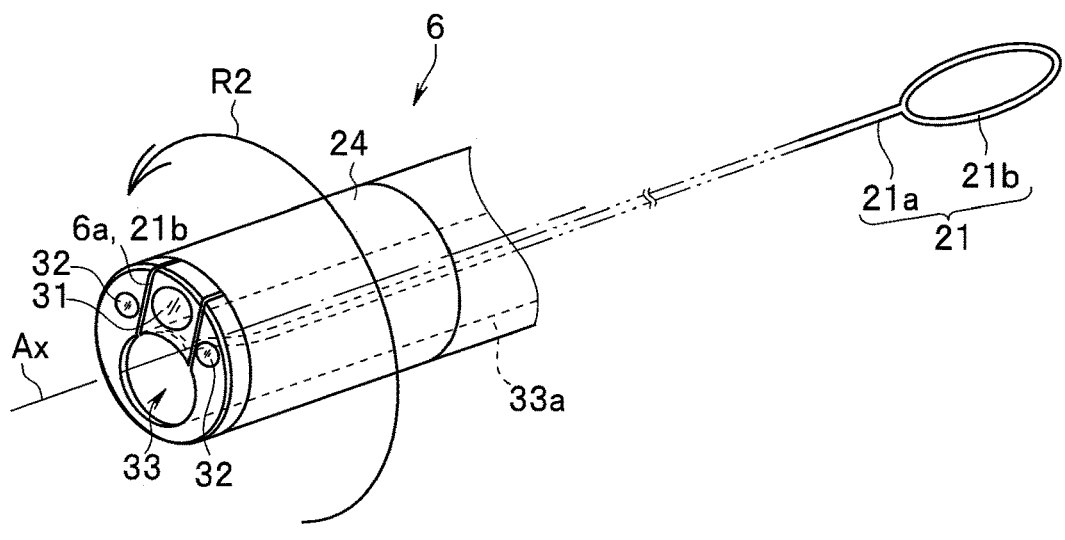
FIG. 6 is a schematic perspective view showing an assembly completion state of the distal end portion of the endoscope shown in FIG. 3 (a coupling-thread fixed state).

As shown in FIGS. 4 to 6, the distal end cover 24 is disposed on the outer periphery surface of the distal end portion 6. To this end, as shown in FIG. 3, a step portion 6c is formed in a predetermined region on the distal end portion 6. The step portion 6c is formed as a recessed step that is one step lower than a maximum outer diameter part of the distal end portion 6. A step height of the step portion 6c is set to be substantially equivalent to a thickness of the distal end cover 24.

An outer diameter of the distal end portion 6 at the part where the step portion 6c is formed is set to be substantially the same as or slightly larger than an inner diameter of the distal end cover 24. A length of the step portion 6c in a direction along the insertion axis (see reference sign Ax in FIG. 3) is set to be substantially equivalent to or slightly greater than a length of the distal end cover 24.

By providing the step portion 6c on the distal end portion 6 in the above manner, the distal end cover 24 may be reliably attached to a predetermined position on the distal end portion 6, and the position may be maintained. When the distal end cover 24 is attached to the step portion 6c of the distal end portion 6, an outer periphery surface of the maximum outer diameter part of the distal end portion 6 and an outer periphery surface of the distal end cover 24 become substantially a same surface. Accordingly, an outer surface of the distal end portion 6 is formed to be substantially flat even in a state where the distal end cover 24 is attached to the distal end portion 6 of the insertion section 9 of the endoscope 2. Accordingly, ease of insertion of the insertion section 9 of the endoscope 2 is not reduced by the distal end portion 6 to which the distal end cover 24 is attached, and smooth insertion may be performed.

Note that in a state where the distal end cover 24 is attached to a predetermined position (the step portion 6c) of the distal end portion 6, at least a part of the distal end cover 24 moves on the outer surface of the distal end portion 6. In the present embodiment, in a state of being attached to the distal end portion 6, the distal end cover 24 is wholly and freely turnable around the insertion axis Ax.

In the state where the distal end cover 24 is attached to the predetermined position of the distal end portion 6, the side surface groove 6b on the distal end portion 6 is covered by the distal end cover 24. Accordingly, when the distal end cover 24 is disposed at a position that covers the groove 6b in a state where the coupling portion 21b is fitted in the side surface groove 6b, the coupling portion 21b of the coupling thread 21 is fixed.

Note that, as shown in FIGS. 3 to 5, a cutout part 24a is formed in the distal end cover 24. The cutout part 24a is formed by cutting out a part of an outer edge portion of the distal end cover 24 on a side close to the distal end. The cutout part 24a is a structural part for releasing a fixed state between the coupling portion 21b on the distal end side of the coupling thread 21 and the distal end portion 6. For this purpose, the cutout part 24a is formed to have an area (first area) that is substantially equivalent to or larger than an area (second area) of a region where the side surface groove 6b is provided. Furthermore, in this case, the cutout part 24a is formed to have a shape that is substantially similar to a shape of the region where the side surface groove 6b is formed. The cutout part 24a may correspond to the shape of the region where the side surface groove 6b is formed.

According to such a configuration, when the distal end cover 24 is turned around the insertion axis Ax in the state where the distal end cover 24 is attached to the distal end portion 6, the distal end cover 24 may be switched between a fixed position at which the region of the side surface groove 6b is covered and the coupling portion 21b is fixed (see a state shown in FIG. 6, first state), and a release position at which the cutout part 24a and the region of the side surface groove 6b match and fixation of the coupling portion 21b is released (see a state shown in FIG. 5, second state).

An attachment method of attaching the endoscopic ligator 20 to the endoscope 2 of the endoscope system 1 according to the present embodiment configured in the above manner will be described below with reference to FIGS. 7 to 12, in addition to FIGS. 3 to 6 used in the description given above.

Figure 7:
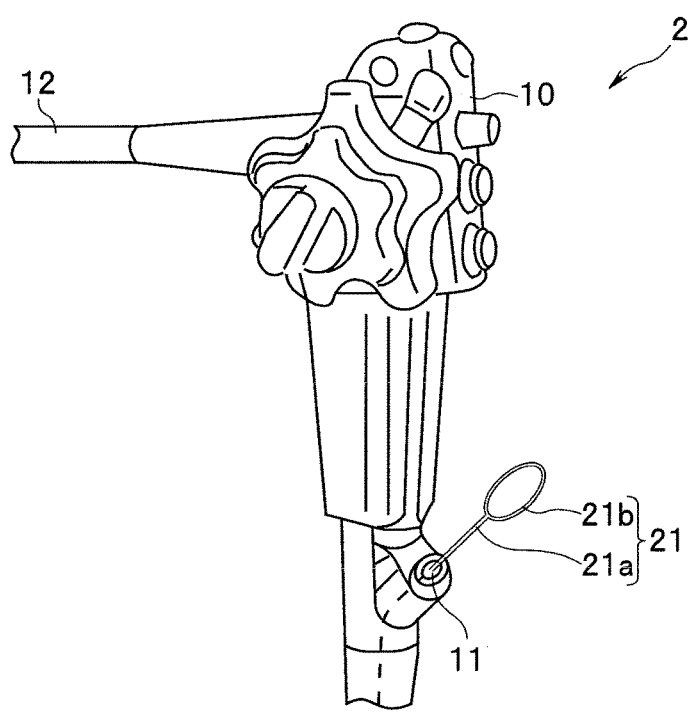
FIG. 7 is a schematic perspective view showing an operation section side when the distal end portion of the endoscope is in the state shown in FIG. 4 (a coupling-thread inserted state).
Figure 8:
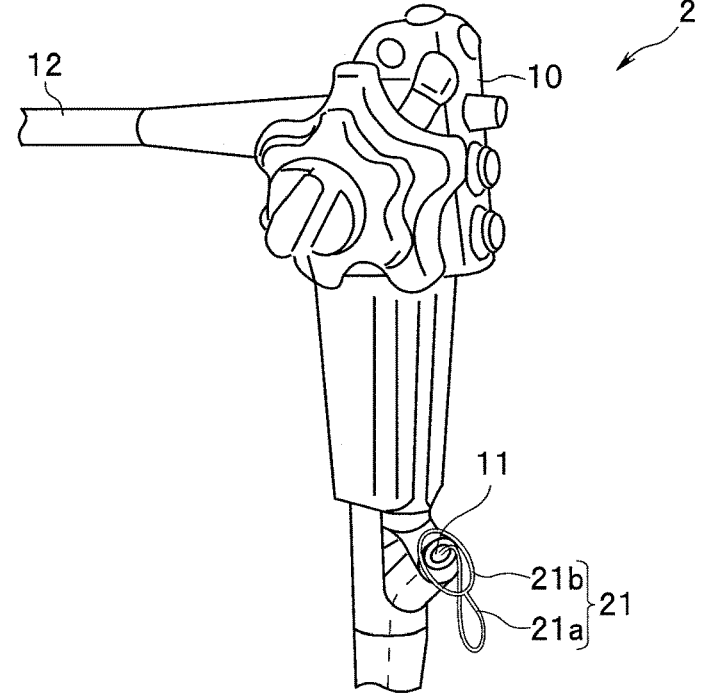
FIG. 8 is a schematic perspective view showing a state on the operation section side when the coupling thread is fastened to a forceps port after a state in FIG. 7.
Figure 11:
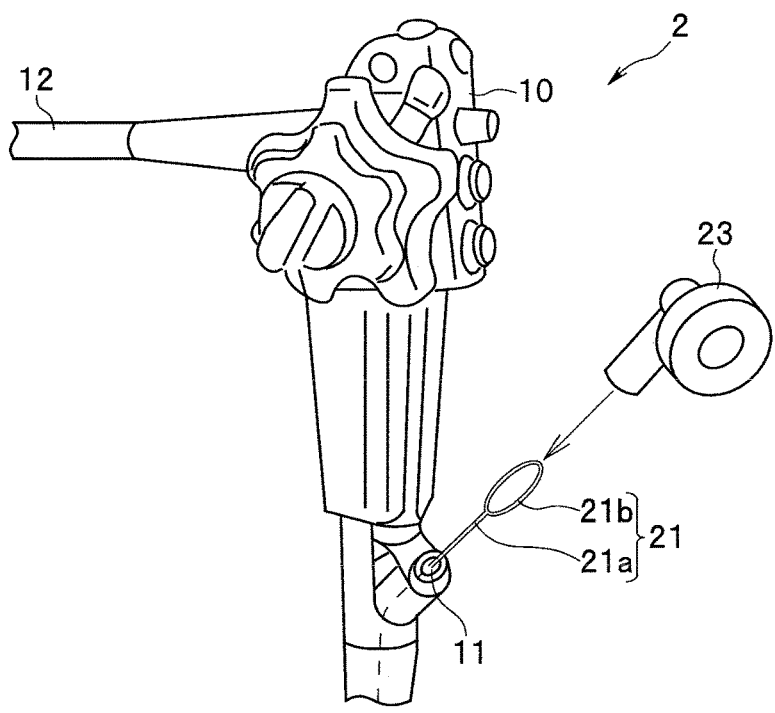
FIG. 11 is a schematic perspective view showing a manner of attaching a winder to an operation section.
Figure 12:
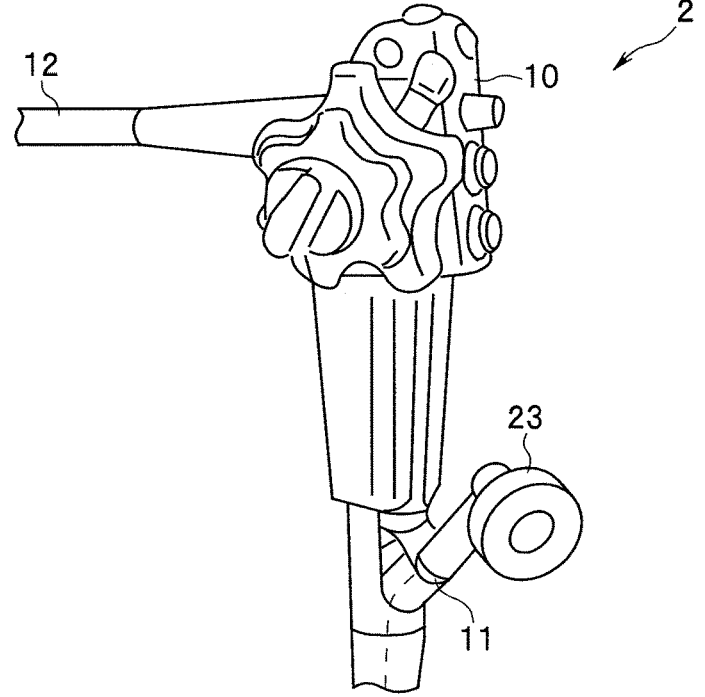
FIG. 12 is a schematic perspective view showing a state where the winder is attached to the operation section.

FIG. 7 is a schematic perspective view showing an operation section side when the distal end portion of the endoscope is in the state shown in FIG. 4 (a coupling-thread inserted state). FIG. 8 is a schematic perspective view showing a state on the operation section side when the coupling thread is fastened to the forceps port after the state in FIG. 7. FIG. 9 is a schematic perspective view showing a manner of coupling the distal end head to the coupling thread. FIG. 10 is a schematic perspective view showing a manner of attaching the distal end head to the distal end portion of the endoscope. FIG. 11 is a schematic perspective view showing a manner of attaching the winder to the operation section. FIG. 12 is a schematic perspective view showing a state where the winder is attached to the operation section.

First, before use of the endoscope 2 of the endoscope system 1, the distal end portion 6 is assumed to be in a state shown in FIG. 3. The distal end cover 24 is attached in this state to the predetermined position on the distal end portion 6. At this time, as shown in FIG. 4, the cutout part 24a of the distal end cover 24 is at a position that matches the region where the side surface groove 6b is provided. Accordingly, the side surface groove 6b is exposed to outside from the cutout part 24a.

Next, the coupling thread 21 is inserted through the treatment instrument insertion channel 33a of the insertion section 9 of the endoscope 2. At this time, as shown in FIG. 4, the partial region on the distal end of the coupling thread 21 (the coupling portion 21b on the distal end side) is disposed at a position protruding outside from the channel opening 33. Furthermore, at this time, as shown in FIG. 7, the coupling portion 21b on the proximal end side of the coupling thread 21 is disposed at a position protruding outside from the forceps port 11.

Next, the coupling portion 21b on the distal end side of the coupling thread 21 is moved in a direction indicated by an arrow 51 in FIG. 4, and the coupling portion 21b in question is fitted in the grooves (6a, 6b) provided on the distal end portion 6. The proximal end side of the coupling thread 21 is pulled in this state in an arrow X direction in FIG. 4. The coupling portion 21b is thereby securely fitted in the grooves (6a, 6b).

Next, the coupling portion 21b on the distal end side of the coupling thread 21 is fixed to the distal end portion 6 of the insertion section 9 using the distal end cover 24 provided on the distal end portion 6. In other words, the distal end cover 24 is turned around the insertion axis Ax in an arrow R1 direction in FIG. 5, and a position of the cutout part 24a in a circumferential direction is moved. The coupling portion 21b fitted in the side surface groove 6b is thus covered by the distal end cover 24. The coupling portion 21b is thereby fixed to the distal end portion 6.

Now, as shown in FIG. 8, the coupling portion 21b on the proximal end side of the coupling thread 21 is provisionally fixed in a state of being fastened to the forceps port 11. Such a state enables the endoscope 2 to be normally used.

Note that in the case of a single-use endoscope, for example, processes up to here may be performed in a manufacturing process. In the case of a reusable endoscope, the coupling thread 21 and the distal end cover 24 may be detached from the treatment instrument insertion channel 33a and discarded at the time of cleaning the endoscope after use. In this case, after the endoscope is cleaned, a new coupling thread 21 and a new distal end cover 24 are attached to the cleaned endoscope by steps described above.

The tasks are performed by a user such as medical personnel (a surgeon, an assistant or the like), for example.

A user of the endoscope 2 uses the endoscope 2 to which the coupling thread 21 is attached, and identifies a treatment target part by performing observation (normal use of the endoscope) of surroundings of living tissue that is a medical treatment target, inside a body cavity. Then, at the time of performing the EVL treatment on the target part, the insertion section 9 of the endoscope 2 is temporarily removed from the body cavity to attach the endoscopic ligator 20. Then, structural members other than the coupling thread 21, among structural members of the endoscopic ligator 20, are attached to the endoscope 2 that is removed.

To this end, first, the distal end cover 24 of the endoscope 2 that is removed is turned in an arrow R2 direction shown in FIG. 6 around the insertion axis Ax, and the cutout part 24a is brought to a position that matches the grooves (6a, 6b) (a state in FIG. 6 is shifted to a state in FIG. 5). The fixed state between the coupling portion 21b on the distal end side of the coupling thread 21 and the distal end portion 6 is thereby released.

Next, fitting of the coupling portion 21b on the distal end side of the coupling thread 21 in the grooves (6a, 6b) is released from the state described above (the state in FIG. 5), and the coupling portion 21b is pulled out in an arrow S2 direction in FIG. 5. Then, the coupling portion 21b is placed in a state indicated by a dotted line in FIG. 5.

Next, the coupling portion 21b on the distal end side of the coupling thread 21 and the distal end head 22 of the endoscopic ligator 20 are coupled to each other. To this end, as shown in FIG. 9, the coupling portion 22b of the distal end head 22 is inserted through the coupling portion 21b of the coupling thread 21, and then, the main body portion 22a of the distal end head 22 is inserted through the coupling portion 22b of the distal end head 22 (see an arrow R3 direction in FIG. 9). The coupling portion 22b of the distal end head 22 and the coupling portion 21b of the coupling thread 21 are thereby coupled to each other as shown in FIG. 10. In this state, the two are pulled in arrow X1 directions in FIG. 10, and the two are thus securely coupled to each other (not shown). In this state, the distal end head 22 is attached to the distal end surface of the distal end portion 6.

Now, the coupling portion 21b on the proximal end side of the coupling thread 21 is detached from the forceps port 11, and a state shown in FIG. 8 is shifted to a state shown in FIG. 11. Then, the coupling portion 21b on the proximal end side is coupled to a predetermined position on the winder 23. Next, as shown in FIG. 12, the winder 23 is attached to the forceps port 11. Then, the winder 23 is operated, and the coupling thread 21 is wound and a slack of the coupling thread 21 is eliminated. The endoscopic ligator 20 is thereby attached to the endoscope 2.

Then, the insertion section 9 of the endoscope 2 to which the endoscopic ligator 20 is attached is inserted again into the body cavity of the subject. Then, the distal end portion 6 of the insertion section 9 is guided to the treatment target part, and an EVL treatment is performed on the treatment target part.

As described above, according to the embodiment described above, in the endoscope system 1 including the endoscope 2, where the endoscopic ligator 20 is configured to be removable, the coupling thread 21, the distal end head 22, and the winder 23 of the endoscopic ligator 20 are configured as separate bodies. The coupling thread 21 is provided along the insertion section 9 of the endoscope 2 (inside the treatment instrument insertion channel 33a) in advance before use of the endoscope system 1.

In this case, at the time of non-use of the endoscopic ligator 20, the partial region on the distal end of the coupling thread 21 (the coupling portion 21*b* on the distal end side) is fixed to the distal end portion 6 using the distal end cover 24. For this purpose, the grooves (6*a*, 6*b*) are formed on the distal end portion 6. The partial region on the distal end side of the coupling thread 21 (the coupling portion 21*b* on the distal end side) fits in the grooves (6*a*, 6*b*). The distal end of the coupling thread 21 is fixed by the distal end cover 24 covering a part of the grooves (6*a*, 6*b*) where the coupling portion 21*b* on the distal end side of the coupling thread 21 is fitted. The cutout part 24*a* is formed in the distal end cover 24, and when the cutout part 24*a* is brought to the position of the grooves (6*a*, 6*b*), the grooves (6*a*, 6*b*) are exposed to outside, and fixation of the distal end of the coupling thread 21 is released.

According to such a configuration, the coupling thread 21 among the structural members of the endoscopic ligator 20 in the endoscope system 1 of the present embodiment may be disposed in advance to pass through the treatment instrument insertion channel 33*a* before use.

Accordingly, in a situation where the endoscopic ligator 20 is to be attached to the endoscope 2 that is being used, immediately before performing an EVL treatment (endoscopic variceal ligation), because the coupling thread 21 is inserted through the treatment instrument insertion channel 33*a* in advance, a step of inserting the coupling thread 21 in the treatment instrument insertion channel 33*a* where a residue or the like is attached due to use of the endoscope 2 may be omitted.

The fixed state of the distal end (the coupling portion 21*b*) of the coupling thread 21 that is fixed to the distal end portion 6 may be easily released by a simple operation of turning the distal end cover 24.

Furthermore, the distal end head 22 and the coupling thread 21 may be easily coupled to each other simply by a task of coupling the coupling portion 22*b* of the distal end head 22 to the coupling portion 21*b* that is pulled out.

Accordingly, a time period when a treatment that uses the endoscope system 1 is interrupted to attach the endoscopic ligator 20 to the endoscope 2 may be greatly reduced. This can contribute to reducing a time period of a treatment that is performed using the endoscope system 1.

Furthermore, as described above, the step of inserting the coupling thread 21 into the treatment instrument insertion channel 33*a* of the endoscope 2 that is being used may be omitted, which can contribute to enhancing hygiene.

Note that with the endoscope system 1 of the embodiment of the present disclosure, the distal end cover 24, at least a part of which moves on the outer surface of the distal end portion 6, is provided on the distal end portion 6 of the insertion section 9. As a specific example configuration, the embodiment described above describes an example where the distal end cover 24 is wholly turnable around the insertion axis Ax, and where the cutout part 24*a* is formed at a part of the distal end cover 24.

According to such a configuration, it is possible to switch between the fixed state where the distal end cover 24 covers the coupling portion 21*b* on the distal end side of the coupling thread 21 fitted in the side surface groove 6*b* of the distal end portion 6 and a fixation released state where the coupling portion 21*b* in question is exposed from the cutout part 24*a* of the distal end cover 24, simply by turning the entire distal end cover 24 around the insertion axis Ax on the outer surface of the distal end portion 6.

As described above, at least a part of the distal end cover 24 moves on the outer surface of the distal end portion 6, and thus, the example configuration described above is not restrictive.

For example, the distal end cover 24 may be freely movable in the direction along the insertion axis Ax. In the case of such a configuration, the fixed state where the side surface groove 6*b* is covered may be released by causing a part of the distal end cover 24 to be placed in a compressed state by elasticity of the distal end cover 24. Accordingly, the cutout part 24*a* does not have to be provided in the case of such a configuration.

Figure 13:
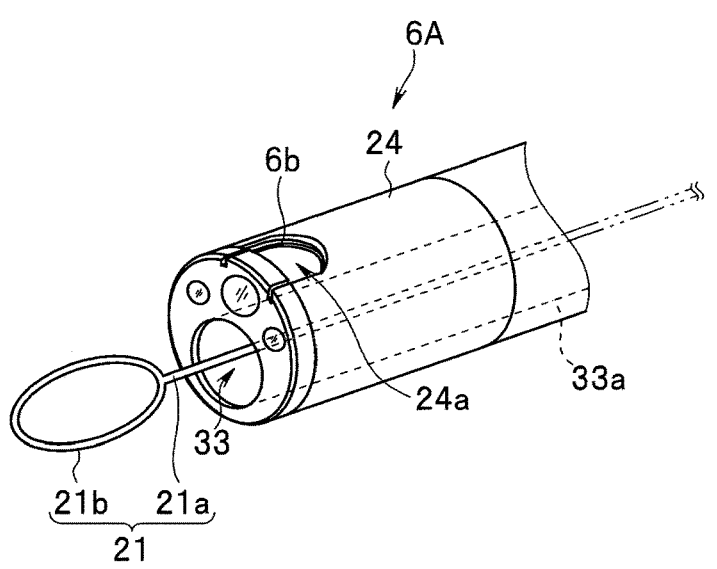
FIG. 13 is a schematic perspective view showing a first modification (the distal end portion) of the endoscope system of the embodiment of the present disclosure.

In the embodiment described above, an example configuration is described where the grooves formed on the distal end portion 6 are the distal end grooves 6*a* and the side surface groove 6*b*, but such a configuration is not restrictive. For example, FIG. 13 is a schematic perspective view showing a first modification of the endoscope system of the embodiment of the present disclosure. The first modification is a modification related to the distal end portion of the endoscope.

As shown in FIG. 13, a distal end portion 6A may be provided with only the side surface groove 6*b* while eliminating the distal end grooves 6*a* of the distal end portion 6 according to the embodiment described above. Exactly the same operations and advantageous effects as in the embodiment described above may be obtained by the distal end portion 6A having such a configuration.

Figure 14:
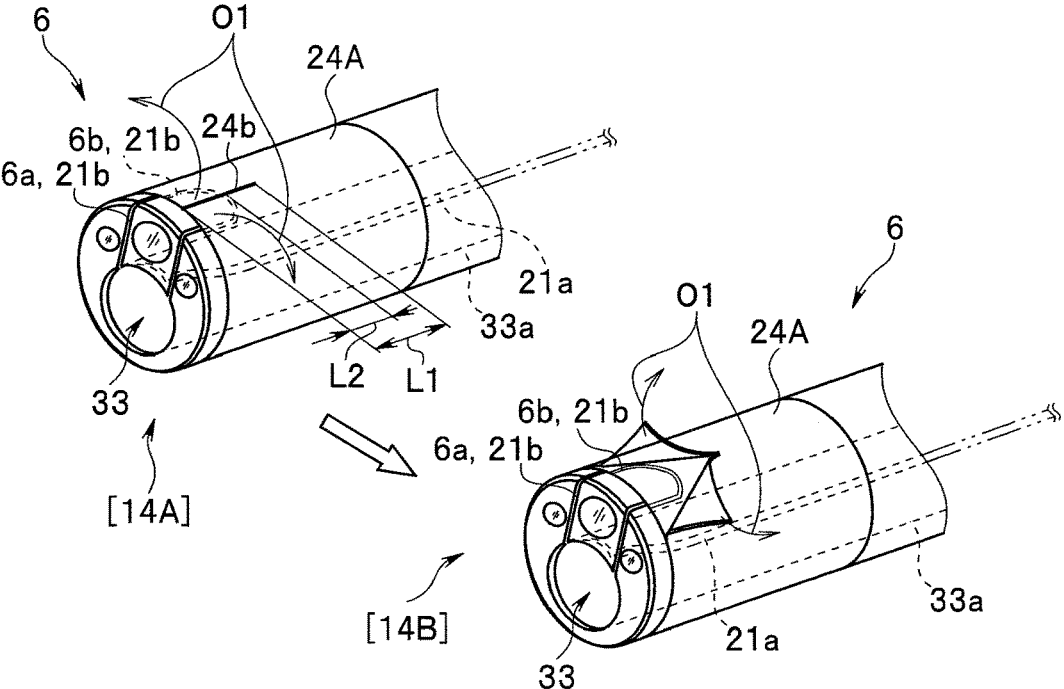
FIG. 14 is a schematic perspective view showing a second modification (a distal end cover) of the endoscope system of the embodiment of the present disclosure.

As an example configuration of the distal end cover 24, the embodiment described above describes an example configuration where the cutout part 24*a* is provided, but such an example configuration is not restrictive. For example, FIG. 14 is a schematic perspective view showing a second modification of the endoscope system of the embodiment of the present disclosure. The second modification is a modification related to the distal end cover provided on the distal end portion of the endoscope.

As shown in FIG. 14, a distal end cover 24A is formed by including, instead of the cutout part 24*a* of the distal end cover 24 of the embodiment described above, one slit 24*b* that extends in the direction along the insertion axis Ax from an edge portion on a distal end side. In this case, the slit 24*b* of the distal end cover 24A includes a function of releasing the fixed state between the partial region on the distal end of the coupling thread 21 (the coupling portion 21*b* on the distal end side) and the distal end portion 6.

Note that a state indicated by reference sign 14A in FIG. 14 shows a fixed state where the coupling portion 21*b* on the distal end side of the coupling thread 21 is fixed by the distal end cover 24A. A state indicated by reference sign 14B in FIG. 14 shows a fixation released state where fixation of the coupling portion 21*b* on the distal end side of the coupling thread 21 by the distal end cover 24A is released.

To this end, the slit 24*b* of the distal end cover 24A has a length (see reference sign L1 in FIG. 14) that is equal to or greater than a length (see reference sign L2 in FIG. 14), in a longitudinal axis (insertion axis Ax) direction, of a part where the partial region on the distal end of the coupling thread 21 (the coupling portion 21*b* on the distal end side) is fixed to the distal end portion 6.

With the distal end cover 24A configured in the above manner, the side surface groove 6*b* may be exposed by rolling up both side edge portions of the slit 24*b* in directions indicated by reference sign O1 in FIG. 14. In other words, fixation of the coupling portion 21*b* to the distal end portion 6 by the distal end cover 24A may be released by moving a part of the distal end cover 24A on the outer surface of the distal end portion 6. Accordingly, same operations and advantageous effects as in the embodiment described above may be obtained by such an example configuration.

Figure 15:
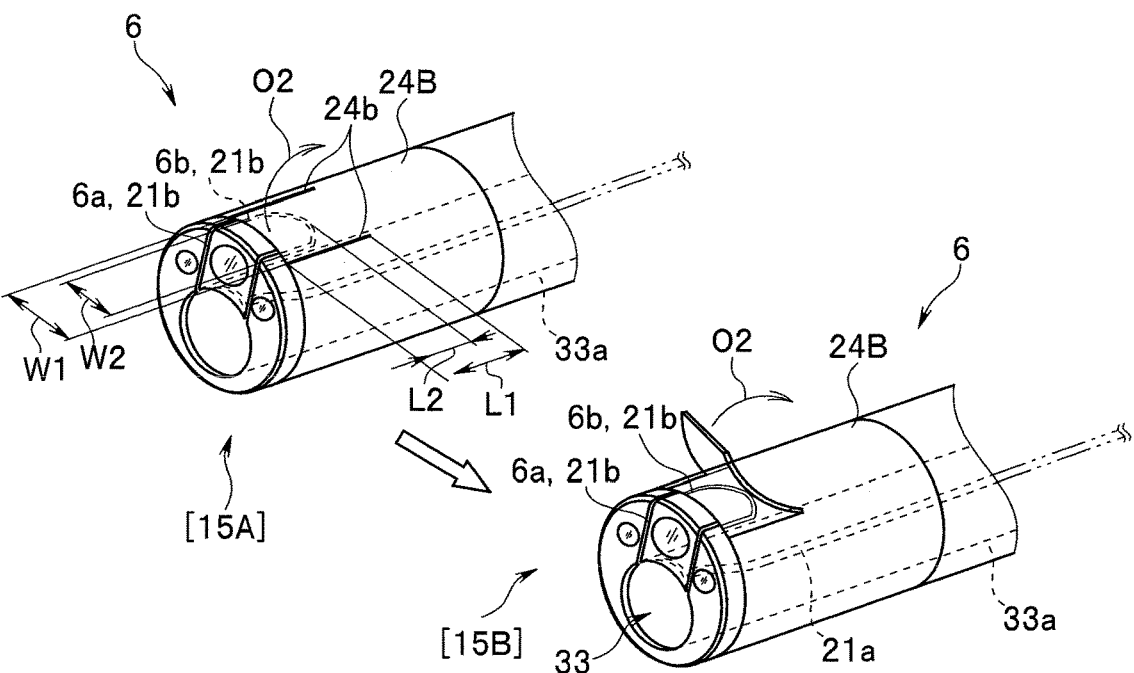
FIG. 15 is a schematic perspective view showing a third modification (the distal end cover) of the endoscope system of the embodiment of the present disclosure.

Furthermore, for example, FIG. 15 is a schematic perspective view showing a third modification of the endoscope system of the embodiment of the present disclosure. The third modification is another modification related to the distal end cover provided on the distal end portion of the endoscope.

An example configuration shown in FIG. 15 is another example configuration of providing a slit to the distal end cover. In the example configuration shown in FIG. 15, a distal end cover 24B is provided with two slits 24b. The two slits 24b each extend from an edge portion on a distal end side of the distal end cover 24B in the direction along the insertion axis Ax, and the two slits 24b are formed with a predetermined gap between the two in a circumferential direction of the distal end cover 24B.

Note that a state indicated by reference sign 15A in FIG. 15 shows a fixed state where the coupling portion 21b on the distal end side of the coupling thread 21 is fixed by the distal end cover 24B. A state indicated by reference sign 15B in FIG. 15 shows a fixation released state where fixation of the coupling portion 21b on the distal end side of the coupling thread 21 by the distal end cover 24B is released.

In this case, a length (see reference sign L1 in FIG. 15) of the two slits 24b in the longitudinal axis (insertion axis Ax) direction (first length) is set to be substantially equivalent to a length (see reference sign L2 in FIG. 15) of the side surface groove 6b in the longitudinal axis (insertion axis Ax) direction (second length) or greater than the length L2 of the side surface groove 6b. A gap (see reference sign W1 in FIG. 15) between the two slits 24b in the circumferential direction is set greater than a gap (see reference sign W2 in FIG. 15) of the side surface groove 6b in the circumferential direction.

With the distal end cover 24B configured in the above manner, the side surface groove 6b may be exposed by rolling up a part of the distal end cover 24B between the two slits 24b in a direction indicated by reference sign O2 in FIG. 15. In other words, fixation of the coupling portion 21b to the distal end portion 6 by the distal end cover 24B may be released by moving a part of the distal end cover 24B on the outer surface of the distal end portion 6. Accordingly, same operations and advantageous effects as in the embodiment described above may be obtained by such an example configuration.

Now, with the endoscope system 1 of the embodiment described above, the coupling thread is inserted and disposed in the treatment instrument insertion channel of the endoscope. An example configuration is described in relation to the endoscope system 1, according to which the coupling thread 21 is used as a structural member of the endoscopic ligator 20.

However, other than being used as a structural member of the endoscopic ligator 20, the coupling thread that is provided along the insertion section of the endoscope may also be applied to a procedure based on a clip-with-line method in an ESD treatment, for example.

Figure 16:
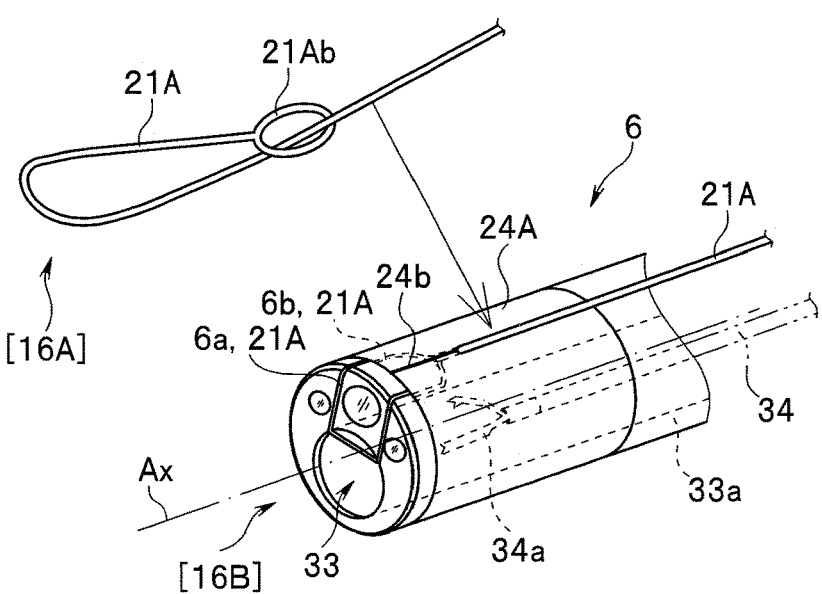
FIG. 16 is a schematic perspective view of the distal end portion showing an example application of the coupling thread of the endoscope system of the embodiment of the present disclosure.

FIG. 16 is a schematic perspective view of the distal end portion showing an example application of the coupling thread of the endoscope system of the embodiment of the present disclosure. Note that reference sign 16A in FIG. 16 extracts and indicates only the coupling thread. Reference sign 16B in FIG. 16 shows a state where the coupling thread is attached to the distal end portion.

In an example application shown in FIG. 16, an endoscope including a distal end portion having the same con-figuration as the configuration in the second modification shown in FIG. 14 is used, for example. Accordingly, the configuration of the distal end portion itself of the endoscope is as described above. Moreover, in this case, a coupling thread 21A is disposed along the insertion section 9 on an outer periphery side, instead of being inserted through the treatment instrument insertion channel 33a of the insertion section 9.

The coupling thread 21A used in the example application has a configuration that is slightly different from the con-figuration of the coupling thread described in the embodi-ment and each modification described above. As indicated by reference sign 16A in FIG. 16, a ring-shaped fastening portion 21Ab is formed at a distal end of the coupling thread 21A. A proximal end side of the coupling thread 21A is inserted through the ring-shaped fastening portion 21Ab of the coupling thread 21A.

A partial region on a distal end of the coupling thread 21A configured in the above manner is fitted in the grooves (6a, 6b) of the distal end portion 6, as indicated by reference sign 16B in FIG. 16. In this state, the partial region on the distal end of the coupling thread 21A is fixed to the distal end portion 6 by the distal end cover 24A. At this time, a part of the coupling thread 21A that is closer to a proximal end than the partial region on the distal end extends to outside of the distal end cover 24A through the slit 24b.

As indicated by reference sign 16B in FIG. 16, in a state where the coupling thread 21A is fitted in the grooves (6a, 6b) of the distal end portion 6, a part, in the partial region on the distal end of the coupling thread 21A, that is different from the part that is fitted in the grooves (6a, 6b) and that is disposed on the distal end surface of the distal end portion 6 is disposed extending across and joining parts of an outer periphery edge portion of the treatment instrument insertion channel opening 33. At this time, the part on the distal end of the coupling thread 21A is disposed while forming a gap to the outer periphery edge portion of the treatment instru-ment insertion channel opening 33.

Note that although not shown, the coupling portion 21b may be formed on the proximal end side of the coupling thread 21A in the same way as with the coupling thread described in the embodiment described above, for example, but such a coupling portion 21b does not have to be formed. The proximal end side of the coupling thread 21A may at least be coupled to a predetermined treatment instrument.

According to such a configuration, the coupling thread 21A may also be applied to a procedure based on the clip-with-line method in an ESD treatment. An operation at the time of performing the procedure based on the clip-with-line method in an ESD treatment using the endoscope system including the endoscope provided with the distal end portion shown in FIG. 16 will be briefly described below.

First, as indicated by reference sign 16B in FIG. 16, the partial region on the distal end of the coupling thread 21A is fixed to the distal end portion 6 of the endoscope. A part of the coupling thread 21A other than a fixed part is disposed along an outer surface of the insertion section of the endo-scope, up to the operation section of the endoscope.

The endoscope in this state is inserted into a body cavity by a normal operation method, and the distal end portion 6 is guided to a treatment target part. In a state where the front surface of the distal end portion 6 is disposed at a position that faces the treatment target part, a treatment instrument 34 including a hemostatic clip 34a (see reference sign 16B in FIG. 16) at a distal end is inserted from the forceps port 11 of the operation section 10 and is inserted through the treatment instrument insertion channel 33a.

Then, at the time of causing the hemostatic clip 34*a* to protrude outside from the treatment instrument insertion channel opening 33, the hemostatic clip 34*a* is slightly opened as indicated by reference sign 16B in FIG. 16. Then, one arm of the hemostatic clip 34*a* in an open state is inserted through the gap between the coupling thread 21A and the outer periphery edge portion of the treatment instrument insertion channel opening 33. The hemostatic clip 34*a* is thus hooked to the coupling thread 21A. The hemostatic clip 34*a* is then placed in a closed state.

When the treatment instrument 34 is moved forward in the insertion axis Ax direction while keeping the state described above, the coupling thread 21A proceeds in a same direction together with the hemostatic clip 34*a*. A fitted state between the coupling thread 21A and the grooves (6*a*, 6*b*) is thereby released. When the coupling thread 21A is further pulled forward, the coupling thread 21A slips through the slit 24*b* to be separated from the distal end cover 24A.

Furthermore, when the coupling thread 21A is further pulled forward, the ring-shaped fastening portion 21Ab of the coupling thread 21A is placed in a fastened state. The coupling thread 21A and the hemostatic clip 34*a* are thereby securely coupled to each other.

In this state, the treatment instrument 34 is operated and the hemostatic clip 34*a* is clipped to a part of living tissue. Then, the hemostatic clip 34*a* is detached from the treatment instrument 34. The hemostatic clip 34*a* is thereby caused to remain inside the body cavity. Also in this state, the hemostatic clip 34*a* is coupled to the coupling thread 21A. Accordingly, by pulling the coupling thread 21A from the hand side at this time, the living tissue clipped by the hemostatic clip 34*a* may be pulled toward the hand side. Then, the procedure based on the clip-with-line method in the ESD treatment may be performed as appropriate.

As described above, the coupling thread of the endoscope system of the embodiment of the present disclosure may be applied not only to the EVL treatment but also to other procedures such as the ESD treatment, for example.

Note that in the example application described above with reference to FIG. 16, a part of the coupling thread that is fixed to the distal end portion is disposed to block a part of the treatment instrument insertion channel opening. According to such a configuration, the hemostatic clip may be easily hooked by a simple operation of inserting the treatment instrument through the treatment instrument insertion channel. However, according to the example configuration shown in FIG. 16, a part of the coupling thread blocks a part of the treatment instrument insertion channel opening at all times. Accordingly, at the time of non-use of the coupling thread, a treatment or a medical procedure that is performed using a treatment instrument that is inserted through the treatment instrument insertion channel is possibly restricted.

Figure 17:
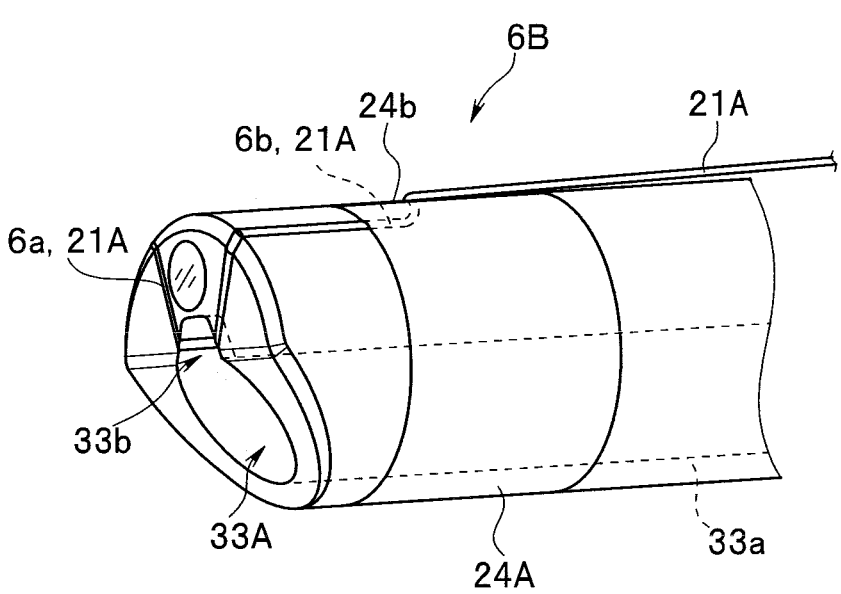
FIG. 17 is a schematic perspective view of the distal end portion showing a modification of the example application in FIG. 16.

Accordingly, with an example configuration of the distal end portion shown in FIG. 17, the coupling thread is prevented from blocking the treatment instrument insertion channel opening. FIG. 17 is a schematic perspective view of the distal end portion showing a modification of the example application shown in FIG. 16.

A basic configuration of a distal end portion 6B in the modification is substantially the same as the configuration of the distal end portion shown in FIG. 16 described above. The distal end portion 6B of the present modification includes a sloping surface that is formed at a part of a distal end surface, and a treatment instrument insertion channel opening 33A is provided in the sloping surface part. Furthermore, a front surface cutout part 33*b* is provided at a part of the treatment instrument insertion channel opening 33A.

In this case, a front surface grooves 6*a* are formed extending from the front surface cutout part 33*b* toward an outer periphery side in a radial direction. According to such a configuration, a part of the partial region on the distal end of the coupling thread 21A fitted in the grooves (6*a*, 6*b*) is disposed at positions in the front surface cutout part 33*b* to join an outer periphery edge portion. In other words, the coupling thread 21A is disposed while forming a gap with the outer periphery edge portion, within a range of the front surface cutout part 33*b*.

As described above, with the distal end portion 6B shown in FIG. 17, the cutout part 33*b* is provided at a part of the treatment instrument insertion channel opening 33A, and a part of the coupling thread 21A is disposed in the cutout part 33*b*. According to such a configuration, the treatment instrument insertion channel opening 33A is not blocked by the coupling thread 21A that is fixed to the distal end portion 6B. Accordingly, regular treatments and medical treatment procedures that are performed using a treatment instrument that is inserted through the treatment instrument insertion channel opening 33A may be prevented from being restricted.

The present disclosure is not limited to the embodiment and each modification described above, and various modifications and applications may, of course, be made within the scope of the gist of the disclosure. Furthermore, the embodiment and each modification described above include disclosures at various stages, and various disclosures may be extracted by combining a plurality of disclosed structural requirements as appropriate. For example, in the case where a problem to be solved by the disclosure may be solved and advantageous effects of the disclosure may be obtained even when some of the structural requirements are removed from all the structural requirements indicated in the embodiment described above, a configuration excluding such structural requirements may be extracted as a disclosure. Moreover, structural elements of the embodiment and each modification may be combined as appropriate. The disclosure is not limited by any specific embodiment, and is limited only by the appended claims.

What is claimed is:

1. An endoscope system, comprising:
an endoscope; and
an endoscope attachment,
wherein the endoscope attachment includes:
a distal end cover configured to be attached on a distal end portion of an insertion section of an endoscope, and
a coupling thread configured to move between a first state and a second state,
wherein the coupling thread includes;
a coupling portion at a distal end of the coupling thread, and
a thread portion extending proximally from the coupling portion,
wherein the distal end cover is attached on to the distal end portion of the insertion section of the endoscope,
wherein the distal end portion includes a groove,
wherein, in the first state;
a distal portion of the coupling portion contacts an inner circumferential surface of the distal end cover, and
the distal portion of the coupling portion is attached to the groove,
wherein the distal end cover includes a slit having a first length,
wherein a length in a longitudinal axis direction that the distal portion of the coupling portion is attached to the distal end portion of the insertion section defines a second length, and wherein the first length is equivalent to or greater than the second length.

2. The endoscope system according to claim 1, wherein the groove is located on one or more of a circumferential side surface of the distal end portion or a distal end surface of the distal end portion.

3. The endoscope system according to claim 1, wherein the distal end cover includes a cutout portion, and wherein an area of the cutout portion is a first area, an area of the groove on a circumferential side surface of the distal end portion is a second area, and a size of the first area is equivalent to or larger than a size of the second area.

4. The endoscope system according to claim 3, wherein, in the first state, the distal portion of the coupling portion is attached to the distal end portion, wherein, in the second state, the distal portion of the coupling portion is released from the distal end portion, and wherein the distal end cover is movable relative to a circumferential side surface of the distal end portion to change between the first state and the second state.

5. The endoscope system according to claim 3, wherein the cutout portion has a shape corresponding to a shape of a region on the circumferential side surface of the distal end portion where the groove is provided.

6. The endoscope system according to claim 3, wherein the distal end cover rotates around an insertion axis of the insertion section relative to the distal end portion to change between the first state and the second state.

7. The endoscope system according to claim 1, wherein, in the first state, a proximal end of the coupling thread is inserted through a treatment instrument channel of the insertion section.

8. The endoscope system according to claim 1, wherein, in the first state, the distal end of the coupling thread is on an outer surface of the insertion section.

9. The endoscope system according to claim 1, wherein, in the first state, a position of the distal portion of the coupling thread in a radial direction relative to a longitudinal axis of the insertion section is between an outer surface of the insertion section of the endoscope and the inner circumferential surface of the distal end cover.

10. An endoscope system, comprising:

an endoscope; and an endoscope attachment, wherein the endoscope attachment includes:

a distal end cover configured to be attached on a distal end portion of an insertion section of an endoscope, and a coupling thread configured to move between a first state and a second state, wherein the coupling thread includes;

a coupling portion at a distal end of the coupling thread, and a thread portion extending proximally from the coupling portion, wherein the distal end cover is attached on to the distal end portion of the insertion section of the endoscope, wherein the distal end portion includes a groove, wherein, in the first state;

a distal portion of the coupling portion contacts an inner circumferential surface of the distal end cover, and the distal portion of the coupling portion is attached to the groove, wherein the distal end cover includes a slit having a first length, wherein a longest part of the groove in a longitudinal axis direction of the insertion section defines a second length, and wherein the first length is equivalent to or greater than the second length.

11. The endoscope system according to claim 10, wherein the groove is located on one or more of a circumferential side surface of the distal end portion or a distal end surface of the distal end portion.

12. The endoscope system according to claim 10, wherein the distal end cover includes a cutout portion, and wherein an area of the cutout portion is a first area, an area of the groove on a circumferential side surface of the distal end portion is a second area, and a size of the first area is equivalent to or larger than a size of the second area.

13. The endoscope system according to claim 12, wherein, in the first state, the distal portion of the coupling portion is attached to the distal end portion, wherein, in the second state, the distal portion of the coupling portion is released from the distal end portion, and wherein the distal end cover is movable relative to a circumferential side surface of the distal end portion to change between the first state and the second state.

14. The endoscope system according to claim 12, wherein the cutout portion has a shape corresponding to a shape of a region on the circumferential side surface of the distal end portion where the groove is provided.

15. The endoscope system according to claim 12, wherein the distal end cover rotates around an insertion axis of the insertion section relative to the distal end portion to change between the first state and the second state.

16. The endoscope system according to claim 10, wherein, in the first state, a proximal end of the coupling thread is inserted through a treatment instrument channel of the insertion section.

17. The endoscope system according to claim 10, wherein, in the first state, the distal end of the coupling thread is on an outer surface of the insertion section.

18. The endoscope system according to claim 10, wherein, in the first state, a position of the distal portion of the coupling thread in a radial direction relative to a longitudinal axis of the insertion section is between an outer surface of the insertion section of the endoscope and the inner circumferential surface of the distal end cover.

\* \* \* \* \*